United States Patent [19]

Seidel et al.

[11] Patent Number: 4,935,204

[45] Date of Patent: Jun. 19, 1990

[54] PROCESS AND DEVICE FOR THE SPECIFIC ADSORPTION OF HEPARIN

[75] Inventors: Dietrich Seidel, Göttingen; Wolfgang Feller, Melsungen; Gerhard Rosskopf, Fuldabrück-Dörnhagen, all of Fed. Rep. of Germany

[73] Assignee: B. Braun-SSC AG, Emmenbrucke, Switzerland

[21] Appl. No.: 271,368

[22] Filed: Nov. 14, 1988

Related U.S. Application Data

[63] Continuation of Ser. No. 149,905, Jan. 28, 1988, abandoned, which is a continuation of Ser. No. 744,197, Jun. 13, 1985, abandoned.

[30] Foreign Application Priority Data

Jun. 16, 1984 [DE] Fed. Rep. of Germany ....... 3422494

[51] Int. Cl.$^5$ ..................... A61K 35/14; C08B 37/10; A61M 37/00
[52] U.S. Cl. ..................... 424/101; 536/21; 604/5; 604/6; 435/803; 210/646; 210/927; 514/822; 514/833
[58] Field of Search ........................ 424/101; 536/21; 604/5,6; 435/803; 210/646, 927; 514/822, 833

[56] References Cited

U.S. PATENT DOCUMENTS

| 3,765,536 | 10/1973 | Rosenberg | 210/927 |
| 4,048,064 | 9/1977 | Clark | 604/5 |
| 4,226,599 | 10/1980 | Butler et al. | 536/21 |

FOREIGN PATENT DOCUMENTS

1195010 6/1965 Fed. Rep. of Germany ........ 536/21

OTHER PUBLICATIONS

A. Thompson et al., J. Lab. Clin. Med., 88: 922–929, 1976.

*Primary Examiner*—John W. Rollins
*Attorney, Agent, or Firm*—Kenyon & Kenyon

[57] ABSTRACT

A process for the specific adsorption of heparin and other heparin-like substances which comprises flowing a buffered solution of whole blood, from which corpuscular blood constituents have been removed, plasma and/or solutions containing whole blood or plasma through an adsorber capsule containing a medium that adsorbs heparin and other heparin-like substances at an acid pH, preferably in the range of 4.0 to 5.5. Preferably, the process is carried out in a closed, extracorporeal circulation and the medium possesses anion exchange resin properties.

35 Claims, 1 Drawing Sheet

PROCESS AND DEVICE FOR THE SPECIFIC ADSORPTION OF HEPARIN

This application is a continuation of application Ser. No. 149,905, filed Jan. 28, 1988 now abandoned which in turn is a continuation of application Ser. No. 744,197 filed June 13, 1985 now abaondoned.

BACKGROUND OF THE INVENTION

Sulfated glycosamino glycan heparin is presently in general clinical use for postoperative subcutaneous thromboembolism prophylaxis in small doses of $3\times5,000$ IU per day. Relatively larger doses of this compound, however, are necessary in the extracorporeal circulation for the prevention of blood coagulation in treatments such as blood oxygenation, surgery using the heart-lung machine, hemodialysis, hemofiltration, hemoperfusion and plasmaphoresis. Moreover, as part of heparin therapy after a thromboembolic condition, i.e., venous thrombosis or pulmonary embolism, heparin salts are administered in daily intravenous doses of 30,000 to 40,000 IU.

After completion of the extracorporeal treatment or in the event that hemorrhagic complications develop during such a treatment, there is often a necessity to neutralize, as quickly as possible, the heparin still circulating in the cardiovascular system which may be present in relatively high concentrations. Promatine sulfate or protamine chloride has traditionally been used for heparin inactivation in such cases. A disadvantage of this treatment, however, according to D. Benayahn et al., Thrombos. Res. 32: 109, 1983, is the occurrence of a rebound phenomenon which can lead to the sudden, renewed release of heparin several hours after neutralization has occurred, particularly in the case of large heparin doses.

In German Offenlegensschrift DE-OS 31 35 814, an extracorporeal precipitation process for the specific separation of low-density lipoproteins (LDL) is described, in which heparin is added to the plasma in a very large dose at an acid pH (pH 5.05 to 5.25) to precipitate a filterable LDL-heparin complex. After the filtration of the heparinized plasma through a separation filter, the pH of the plasma from which the LDL-heparin complex has been removed is adjusted to within the physiological pH range of the patient by passing the plasma through a hemodializer, after which the plasma is administered back into the patient.

A total of approximately 100,000 heparin units/liter, however, are needed for the quantitative precipitation of the LDL-heparin complex in this extracorporeal treatment. Morover, the heparin concentration in the plasma readministered to the patient can reach levels of above 20 IU/ml, causing the patient's plasma level of heparin to reach values of about 4 to 12 IU/ml of plasma, thereby introducing an increased risk of hemorrhage.

Langer, et al. (J. Biol. Chem. 257: 7310, 1982; Sicence 217: 261, 1982) describe a process for the removal of heparin in which plasma is led through an exchanger that immobilizes heparinase from *Flavobacterium heparinum* at its surface. The heparin is broken down enzymatically into fragments that have, in comparison to heparin, a very minor anti-coagulative effect. For a broad application, this process requires, however, that the relatively unstable heparinase enzyme be obtained in large quantities as well as high purity and enzyme activity and that it be capable of being converted into a stable, sterile form that can be stored. Even a direct injection of the purified enzyme for the inactivation of the heparin is presently impossible for the toxicological reasons described by M. D. Klein in *J. Lab. Clin. Md.* 102: 838, 1983.

The binding of heparin to ion exchangers has been known for a relatively long period of time. For example, ion exchanges have been used for years in the isolation of heparin from aqueous solutions for the production of heparin from biological materials as well as for the purification of heparin fragments and heparin fractions, as described in J. P. Green, *Nature* 186: 472, 1960; R. H. Yue, et al., *Thrombos. Haemostas*, 42: 1452 ff., 1979; M. W. Piepkorn, et al., *Thromb. Res.* 13: 1077–1087, 1978, German Offenlegensscrift DE-OS 26 52 272; and German Ofenlegensscrift DE-OS 31 15 245.

The cited publications also contain descriptions of additional efforts to adsorb heparin from blood or blood plasma in the physiological pH range of blood or blood plasma. Due to the basic characteristics of the ion exchanger materials used, however, an undesirable, non-specific binding of plasma proteins must always be expected in the physiological pH range. It has also been observed (E. Schmitt et al., Biomaterials 4: 309–314, 1983, and P. Ferruti et al., Biomaterials 4: 218–221, 1983) that after the binding of heparin to basic anion exchanger materials such as membranes of N,N-dimethylaminoethyl cellulose (DEAE) and poly(amidoamine) resins, a heparin desorption phenomenon can be observed in the physiological pH range.

Thus, there exists a need for a means by which heparin and its derivatives, heparin fractions, heparinoids heparin fragments, and other heparin-like substances can be quickly and substantially removed from plasma without the occurrence of more than a negligible heterogenous absorption of plasma proteins when basic anion exchanger materials of suitable composition are used for the adsorption, and without a risk of occurrence of a rebound phenomenon.

SUMMARY OF THE INVENTION

It is an object of this invention to provide a means for the removal of heparin and other heparin-like substances from the blood after the administration of heparin to a subject for a therapeutic function.

It is another object of this invention to provide a means by which heparin and other heparin-like substances can be quickly and substantially removed from the blood while avoiding the separation of other plasma constituents from the extracorporeal circulation and without the risk of occurrence of the rebound phenomenon.

These and other objects are achieved through the provision of a process for the specific adsorption of heparin and other heparin-like substances from a solution of whole blood, plasma and/or solutions containing whole blood or plasma which comprises separating corpuscular blood constituents from the solution; buffering, by means of a suitable buffer, the solution to an acid pH range, preferably in the range of about 4.0 to 5.5; flowing the buffered solution through an adsorber capsule containing a medium that adsorbs heparin and other heparin-like substances thereby removing a substantial amount of heparin and other heparin-like substances from the buffered solution; and adjusting the pH of the solution to physiological conditions appropriate to a desired subject, such that the solution may be infused safely into the desired subject.

The process according to the invention may further comprise recombining the corpuscular blood constituents with the solution that has been adjusted to a pH corresponding to the physiological conditions of a desired subject, and then infusing the recombined solution into the desired subject or returning the recombined solution to regular stored blood.

The other heparin-like substances that can be removed from the blood or plasma preferably are selected from the group consisting of heparin fractions, heparin fragments, heparin derivatives, heparinoids and polyanionic glycosamino glycan containing sulfate ester groups.

In a preferred embodiment of the process according to the invention, the buffered solution flow through the adsorber capsule at a rate of flow between about 60 ml/hr and 25 L/hr, and the adsorber capsule is filled with a gel possessing anion exchange properties.

The process according to the invention makes use of a device for the specific adsorption of heparin and other heparin-like substances from whole blood, plasma and/or solutions containing whole blood or plasma comprising a housing means composed of physiologically acceptable materials having a cap and bottom surfaces and a central intake nozzle and an outlet nozzle in connection therewith; an ion exchange medium which is situated in the interior of said adsorber capsule that is capable of adsorbing heparin and other heparin-like substances; a feeding line connected to the central intake nozzle; and a draining line connected to said outlet nozzle, whereby whole blood, plasma and/or solutions containing whole blood or plasma containing heparin and/or other heparin-like substances can be passed through the feeding line into the central intake nozzle, through the ion exchange material, out of the outlet nozzle and through the draining line.

In a preferred embodiment of the device according to the invention, the housing means is a cylindrical adsorber capsule, contains screens between about 50 and 100 μm mesh and contains a gel capable of adsorbing heparin and other heparin-like substances.

DETAILED DESCRIPTION OF THE INVENTION

It has surprisingly been discovered that heparin and/or other heparin-like substances such as polyanionic heparin derivatives, water-soluble polymeric, polyanionic heparinoids and sulfated glycosamino glycan can be removed extracorporeally from the blood, blood plasma and/or solutions containing whole blood or plasma at pH values generally in the acid range by specific adsorption with suitable ion exchange materials without previously associated problems such as significant heterogeneous adsorption of plasma proteins.

According to the process of the invention, corpuscular blood constituents and plasma are first separated from one another by known methods performed on whole blood from an extracorporeal circulation or from stored blood, if necessary. The obtained plasma or solutions containing plasma which contain heparin and/or other heparin-like substances is then adjusted to an acid pH, preferably in the range of 4.0 to 5.5, generally by the addition of a suitable buffer. Ideally, the plasma or solutions containing plasma should contain heparin, heparin fractions, or heparinoids in amounts ranging between about 1,000 to 200,000 IU/L, and in the case of heparinoids, heparin fragments, heparin fractions and heparin derivatives, in amounts up to about 2 g/L.

The buffered fluids are then led at a rate of flow between about 60 ml/hr and 25 L/hr through a sterilized, preferably cylindrical, adsorber capsule with a cap and a bottom equipped with central intake and outlet nozzles containing, if needed, circular double screens of 50 to 100 μm mesh. The adsorber capsule further contains a medium, or adsorber material, that adsorbs any or all of the heparin and other heparin-like substances such as heparin derivatives, heparin fractions, heparin fragments heparinoids and sulfated glycosamino glycans. The medium or adsorber material may be moistened with water for optimum effect.

The process according to the invention will ideally cause to be adsorbed 80 to 100% of the heparin and other heparin-like substances originally present in the plasma or solutions containing plasma. The fluids from which heparin and other heparin-like substacnes have been removed may then be subjected to dialysis e.g., employing bicarbonate, to elevate the pH of the plasma to physiological conditions, followed by the recombination of the deheparinized plasma or plasma solution with corpuscular blood constituents (as used herein, the word "heparin" refers to heparin and the other heparin-like substances). Finally, the plasma or plasma solution from which heparin and/or the other heparin-like substances were removed may be reinfused into the patient or otherwise recombined with regular stored blood.

It has been observed that the heparin adsorption and the suppression of heterogeneous adsorption of plasma proteins depends, to a significant degree, upon the ability of the heparin molecules to penetrate the pores of the adsorber material at a pH in the range of about 4.0 to 5.5. Thus, especially suitable materials for the adsorption of heparin and the other heparin-like substacnes are macroporous, high-porosity, hydrophilic anion exchange materials on an acrylate base, which for reasons of chemical stability, preferably contain tertiary amine groups as anchor groups. The physical form of the adsorber materials can be varied as applied to membranes, plates, and gels, as well as granular materials. In one embodiment of the invention, the adsorber capsule contains the adsorber material in the form of a gel that adsorbs heparin and the other heparin-like substances, and employs known techniques to prevent the gel from running out of the adsorber capsule.

The adsorber medium may also be in the form of spherical anion exchange resins consisting of resin spheres with a granule size of between about 100 and 2,000 μm, and preferably, between about 300 and 1,000 μm.

The device for the specific adsorption of heparin and the related heparin substances comprises, according to the invention, a sterilized, preferably cylindrical adsorber capsule with a cap and bottom equipped with central intake and outlet nozzles containing, if needed, circular double screens of between about 50 and about 100 μm mesh. In a preferred embodiment, the adsorber capsules are about 4 to 30 cm long and about 2 to 10 cm in diameter. Through their intake and outlet nozzles and exchangeable feeding and draining lines made of known materials, the adsorber capsules are connected to pumps and monitoring equipment, which control the feeding of the heparinized whole blood or plasma and the withdrawal of the purified fluids.

The sterilized, cylindrical adsorber capsules are made of known, physiologically unobjectionable materials. They are filled with the adsorber medium that adsorbs heparin and other heparin-like substances and acts as an ion exchanger. Under operating conditions, the adsorber medium, which adsorbs heparin and/or the other heparin-like substances, has a capacity for heparin and the related heparin substances of about 5,000 to 400,000 IU, and preferably 10,000 to 100,000 IU/liter, or a corresponding capacity of heparin and related heparin substances of up to about 2 grams. Thus, after the uptake of the given amount of heparin, the adsorption kinetics is slowed down to the extent that little or no adsorption of heparin and related heparin substances occurs while maintaining flow rates of about 60 ml/hr to 25 L/hr.

In another embodiment of the invention, the adsorber capsule contains an adsorption filler cartridge comprising a supporting screen with a solid or hollow core around which screen is wound a fiber mat on a cellulose base that possesses the anion exchange properties and thereby acting as an active adsorber material.

The adsorber capsules containing the adsorbing anion exchange material are sterilized by known methods prior to the commencement of the subject process. For example, adsorber capsules sterilized by treating with gamma-rays, heat, ethylene oxide or other chemical sterilizing agents such as sodium hypochlorite or peroxide solution may be used.

To perform the preferred embodiment of the process according to the invention for the specific adsorption of heparin and the other heparin-like substances, the heparin and/or other heparin-like substances containing solution, whole blood or blood plasma is first fed through a membrane filter to separate out corpuscular constituents by known methods. The resulting solution containing the heparin and/or other heparin-like substances is subsequently adjusted to a pH preferably in the range of about 4.0 to 5.5, and most preferably to a pH between 4.7 and 5.2, by the addition of a buffer. The preferred buffer is sodium acetate since it provides optimal buffering in this pH range. Other physiologically compatible buffer systems active in this pH range can be employed as well.

The buffered fluids containing heparin and/or the other heparin-like substances are ideally fed into the adsorber capsule at a flow rate of about 60 ml/hr to 25 L/hr, and preferably 1.5 to 12 L/hr, with the aid of a pump through suitable lines into the sterilized, cylindrical adsorber capsule described above, which contains the medium for adsorbing heparin and/or the other heparin-like substances. This medium can be, as described above, a resin, a gel or a fiber mat supporting the adsorbing material as well as any other system supporting anion exchange groups which results in sufficient contact between the adsorber medium and the compounds to be adsorbed.

The fluids leaving the adsorber capsule from which the heparin and/or the other heparin-like substances have been removed are subsequently dialyzed, preferably by a bicarbonate dialysis, to elevate the pH to physiological conditions, or those conditions that are compatible with a safe administration of the fluid to a desired patient, after which the fluid and the corpuscular blood constituents are recombined, if needed, and infused into a patient or recombined with regular stored blood.

It is possible to determine the heparin and blood protein concentration before the onset of the adsorption process, during its course and after its conclusion by the use of known methods, e.g., the biuret method. As supported by the individual examples herein, 80 to 100% of the heparin and related heparin substances may be separated from the blood or blood plasma in accordance with the invention process, while the protein concentration before and after adsorption are largely identical. Consequently, the adsorption of heparin and the other related heparin substances, without the heterogenous adsorption of body proteins, is made possible by the process according to the invention.

Another advantage of the process according to the invention is the fact that the use of the basic ion exchange adsorber materials described herein also permit the removal of other polyanionic glycosamino glycans which have a structure comparable to heparin and which contain sulfate ester groups, as well as the derivatives, fractions and breakdown products of such other polyionic glucosamine glucans. Thus, pharmaceutical substances containing polyanionic sulfate groups, e.g. the pharmaceutical SP 54 ® containing anionic sulfate ester, can be eliminated from human plasma in accordance with the invention when the pH of the plasma, e.g. in an extracorporeal circulation, is adjusted to between about 4.0 and 5.5 and led through one of the basic anion exchanger adsorber materials described herein. An almost quantitative adsorption of the compounds carrying sulfate ester to the adsorber materials is achieved while the heterogeneous adsorption of proteins is largely suppressed.

The invention is further illustrated by the following examples.

EXAMPLE I

The adsorption effect of the adsorber materials on heparin was tested as described below:

Human plasma containing 50,000 IU/liter of heparin was mixed with the same volume of a 0.2M acetate buffer (pH 4.88). The resulting lipoprotein-heparin complex was separated by filtration through a filter (0.4 um) in accordance with German Offenlegensschrift DE-OS 31 35 814. This heparin-plasma-acetate mixture was pumped over the adsorber materials, or ion exchanger, to be tested. The protein concentration was measured by the biuret method and the heparin concentration with a test kit by Kabi, according to Teien et al., Thromb. Res. 8: 413, 1976, and Thromb. Res. 10: 399, 1977.

One-hundred milliliters of plasma-acetate solution were pumped at a rate of 50 ml/hr over a 5 ml sample of each of the resin materials listed in Table 1, fractions were collected and their heparin concentrations were determined as described above. The percentage of non-adsorbed heparin is plotted against the volume of the column eluate in FIG. 1.

The adsorber materials were equilibrated with a mixture (1:1) of 0.2M sodium acetate solution, pH 5.12 and 0.9% NaCl-solution.

TABLE 1

| Resins tested for their adsorptive action: | | |
|---|---|---|
| Resin | Type | Source |
| DEAE-Sephacel | Cellulose anion exchanger | Pharmacia Fine Chemicals, Uppsala |

TABLE 1-continued

| Resin | Type | Source |
|---|---|---|
| TEAE-Cellulose | Cellulose anion exchanger | Serva, Heidelberg |
| Lewatit ® CA-9249 | Macroporous anion exchanger | Bayer, AG, Leverkusen |
| AG-MP I | macroporous anion exchanger | BIO-RAD, Munich |
| IRA-900 | porous, strongly basic anion exchanger $-CH_2-N^+(CH_3)_3$ | Serva, Heidelberg |
| IRA-410 | stongly basic anion exchanger $-CH_2-N^+(CH_3)_2$ $\quad\quad\quad \mid$ $\quad\quad\quad CH_2-CH_2-OH$ | Serva, Heidelberg |

The experiments demonstrated that particularly macroporous adsorber materials are highly suitable to almost completely adsorb heparin from plasma at pH 5.1.

The following additional exchanger or adsorber materials were tested with equal success:

Quatodex ®- a quaternary anion exchanger by Pharmacia Fine Chemicals, Uppsala, while the resin matrix is a dextran crosslinked with epichlorhydrin.

Cytodex 1 ®- a tertiary anion exchanger by Pharmacia Fine Chemicals, Uppsala, which has an anchor group of the following structure:

EXAMPLE 2

Other adsorber materials (Zetaprep ®, AMF CUNO, Meriden, Connecticut), consisting of rolled fiber mats on a cellulose base to which DEAE-groups were applied as anchor groups were also tested.

For this purpose, 2,000 ml of pooled human plasma were mixed with a solution of 2,000 ml of 0.2M sodium acetate buffer, pH 4.88/0.9% NaCl-solution (1:1 v/v), to which had been added 50,000 IU/liter of heparin. The lipoprotein-heparin complex was separated by filtration through a 0.4/μm filter.

The filtrate was pumped at a rate of 50 ml/minute through the heparin adsorber, which contained the mentioned Zetaprep ®-fiber mats with DEAE coating as adsorber material. The heparin concentration in the acetate buffer was increased to 100,000 IU/liter in some of the adsorption tests.

| Fiber mat | Source | Covering % | Heparin concentration used in the acetate buffer (IE $.1^{-1}$) |
|---|---|---|---|
| Zepatrep ® 100-1 | AMF-CUNO Meriden, USA | 60 | 50,000 |
| Zepatrep ® 100-2 | " | 60 | 100,000 |
| Zepatrep ® 250-1 | " | 60 | 100,000 |
| Zepatrep ® 250-2 | " | 50 | 100,000 |
| Zepatrep ® 250-3 | " | 40 | 50,000 |

The Zetaprep ® capsules differed in the number of layers of cellulose ion exchanger adsorber material (DEAE) wound in spiral on a core. The commercial capsules corresponded to a covering of 100%. The degree of covering of the capsules used in the these tests was calculated with respect to this maximal covering.

As is apparent from the results in Tables 2 to 6, the total protein concentration before and after the DEAE-Zetaprep ® capsule remained unchanged. The heparin concentration, in contrast, is considerably decreased, or lowered to a no longer measurable level. It is understood that the heparin binding depends on the number of wound layers of ion exchanger adsorber material at a given rate of flow, and that it can be optimized for any rate of flow therefor. The heparin filter Zetaprep ® 250-1 meets the requirements with respect to efficient heparin adsorption and minimal protein adsorption. After the adsorption trial, the exchangers were rinsed with 0.2M sodium acetate buffer, pH 5.11/0.9% NaCl (1:1 v/v) and bound proteins were eluted with 0.2M sodium acetate, pH 4.85, 2M NaCl. The protein determination according to Lowry showed a total protein adsorption of less than 0.5% on the Zetaprep ® capsules.

TABLE 2

| Fraction | Volume ml | Heparin conc. IU/liter | Total heparin IU | Cholesterol g/L | Total protein g/L |
|---|---|---|---|---|---|
| Adsorption test with Zetaprep ® DEAE-100-1: | | | | | |
| The heparin concentration in acetate buffer was 50,000 IU/liter | | | | | |
| Before 0.4 μm filter | 4,000 | 24. | 96,000 | 0.71 | 27.9 |
| After 0.4 μm filter appr. | 4,000 | 13.8 | 55,200 | 0.43 | 25.2 |
| After employment of DEAE-Zetaprep ® FILTER | | | | | |
| 1 | 800 | 0 | 0 | 0.39 | 23.2 |
| 2 | 800 | 0.17 | 136 | 0.41 | 25.4 |
| 3 | 800 | 0.71 | 568 | 0.41 | 25.2 |
| 4 | 880 | 2.00 | 1760 | 0.41 | 25.7 |
| 5 | 520 | 2.55 | 1326 | 0.40 | 25.0 |
| Collected fractions | 3800 | 1.00 | 3800 | 0.41 | 25.7 |

TABLE 3

| Fraction | Volume ml | Heparin conc. IU/liter | Total heparin IU | Cholesterol g/L | Total protein g/L |
|---|---|---|---|---|---|
| Adsortion test with Zetaprep ® DEAE-100-2: | | | | | |
| The heparin concentration in acetate buffer was 50,000 IU/liter | | | | | |

TABLE 3-continued

Adsorption test with Zetaprep ® DEAE-100-2:

| Fraction | Volume ml | Heparin conc. IU/liter | Total heparin IU | Cholesterol g/L | Total protein g/L |
|---|---|---|---|---|---|
| Before 0.4 μm filter | 4,000 | 23.5 | 94,000 | 0.73 | 27.2 |
| After 0.4 μm filter appr. | 4,000 | 14.1 | 56,400 | 0.39 | 24.3 |
| After employment of DEAE-Zetaprep ® FILTER | | | | | |
| 1 | 750 | 0.2 | 150 | 0.36 | 23.6 |
| 2 | 750 | 0.79 | 593 | 0.37 | 24.9 |
| 3 | 750 | 2.35 | 1764 | 0.37 | 24.8 |
| 4 | 750 | 2.90 | 2175 | 0.37 | 25.3 |
| 5 | 800 | 5.25 | 4200 | 0.37 | 25.2 |
| Collected Fractions | 3800 | 2.45 | 9310 | 0.36 | 25.0 |

TABLE 4

Adsorption test with Zetaprep ® DEAE-250-1:

| Fraction | Volume ml | Heparin conc. IU/liter | Total heparin IU | Cholesterol g/L | Total protein g/L |
|---|---|---|---|---|---|
| The heparin concentration in acetate buffer was 100,000 IU/liter | | | | | |
| Before 0.4 μm filter | 4,000 | 45 | 180,000 | 0.80 | 29.2 |
| After 0.4 μm filter appr. | 4,000 | 22.5 | 90,000 | 0.25 | 25.8 |
| After employment of DEAE-Zetaprep ® FILTER | | | | | |
| 1 | 800 | 0 | 0 | 0.22 | 24.0 |
| 2 | 800 | 0 | 0 | 0.24 | 25.8 |
| 3 | 800 | 0 | 0 | 0.23 | 25.9 |
| 4 | 800 | 0.08 | 64 | 0.22 | 25.7 |
| 5 | 500 | 0.18 | 90 | 0.22 | 26.1 |
| Collected Fractions | 3700 | 0 | — | 0.23 | 26.0 |

TABLE 5

Adsorption test with Zetaprep ® DEAE-250-2:

| Fraction | Volume ml | Heparin conc. IU/liter | Total heparin IU | Cholesterol g/L | Total protein g/L |
|---|---|---|---|---|---|
| The heparin concentration in acetate buffer was 100,000 IU/liter | | | | | |
| Before 0.4 μm filter | 4,000 | 50 | 200,000 | 0.73 | 27.6 |
| After 0.4 μm filter appr. | 4,000 | 23.8 | 95,200 | 0.25 | 24.6 |
| After employment of DEAE-Zetaprep ® FILTER | | | | | |
| 1 | 800 | 0 | 0 | 0.22 | 22.5 |
| 2 | 820 | 0.27 | 221 | 0.23 | 24.2 |
| 3 | 930 | 1.35 | 1256 | 0.23 | 24.2 |
| 4 | 810 | 2.35 | 2904 | 0.23 | 23.9 |
| 5 | 350 | 2.60 | 910 | 0.23 | 24.4 |
| Collected Fractions | 3710 | 1.24 | 4600 | 0.23 | 23.7 |

TABLE 6

Adsorption test with Zetaprep ® DEAE-250-2:

| Fraction | Volume ml | Heparin conc. IU/liter | Total heparin IU | Cholesterol g/L | Total protein g/L |
|---|---|---|---|---|---|
| The heparin concentration in acetate buffer was 100,000 IU/liter | | | | | |
| Before 0.4 μm filter | 4,000 | 22.5 | 90,000 | 0.69 | 27.5 |
| After 0.4 μm filter appr. | 4,000 | 13.5 | 54,000 | 0.43 | 25.0 |
| After employment of DEAE-Zetaprep ® FILTER | | | | | |
| 1 | 800 | 0 | 0 | 0.38 | 22.9 |
| 2 | 800 | 0 | 0 | 0.41 | 25.3 |
| 3 | 800 | <0.1 | — | 0.41 | 23.4 |
| 4 | 870 | 0.29 | 252 | 0.43 | 24.8 |
| 5 | 430 | 0.43 | 185 | 0.42 | 25.7 |
| Collected | 3700 | <0.1 | — | 0.41 | 24.6 |

TABLE 6-continued

Adsorption test with Zetaprep ® DEAE-250-2:

| Fraction | Volume ml | Heparin conc. IU/liter | Total heparin IU | Cholesterol g/L | Total protein g/L |
|---|---|---|---|---|---|
| Fractions | | | | | |

EXAMPLE 3

The exchangers 2058/83, 2059/83 and 2060/83 by Bayer AG, Leverkusen, were tested in an additional adsorption trial and are cross-linked macroporous acrylate resins with tertiary anchor groups.

The mean granule size of the exchangers is recorded in Table 7:

TABLE 7

Granule sizes of the exchange resins on an acrylate base used in Example 3:

| | Mean granule size (μm) | Percentage ≦300 μm |
|---|---|---|
| 2058/83 | 448 | 7 |
| 2059/83 | 273 | 22 |
| 2060/83 | 195 | 47 |

The pretreatment of human plasma with heparin and acetate was performed as described in Example 2.

The exchangers were quilibrated before the trial with 0.2M acetate buffer, pH 5.11/0.9% NaCL (1:1 v/v). The heparin concentration after the separation of the LDL-heparin complex was 18 IU/ml. Aliquots of 100 ml plasma-acetate mixture with heparin were pumped over 5 ml exchanger at a rate of 50 ml/hr.

The results can be found in the following Tables 8 and 9.

TABLE 8

Heparin adsorption and protein adsorption on exchange resins on a base of acrylate.

| ml Plasma/acetate, pH 5.1 (18 IU/ml heparin) | Exchange resin | % Heparin adsorbed | Adsorbed protein (mg) | Unadsorbed (protein/mg) | % Adsorbed protein |
|---|---|---|---|---|---|
| 100 | 2058/83 | 97 | 8.7 | 2,595 | 0.33 |
| 100 | 2059/83 | 99 | 12.5 | 2,595 | 0.48 |
| 100 | 2060/83 | 100 | 13.2 | 2,600 | 0.51 |
| 170 | 2060/83 | 100 | | | |
| 200 | 2060/83 | 100 | | | |

TABLE 9

Protein concentrations and protein electrophoresis of the acetate-plasma mixture before and after ion exchanger 2058.83, 2059/83 and 2060/83

| | Total protein g/dl | Albumin g/dl | Protein electrophoresis | | | |
|---|---|---|---|---|---|---|
| | | | Alb. | α-1 | α-2 | β |
| Plasma | 5.60 | 3.80 | 55.8 | 3.4 | 8.4 | 11.3 | 21.1 |
| before 2058/A | 5.22 | 3.75 | 66.1 | 3.0 | 6.9 | 8.7 | 15.3 |
| after 2058/A | 5.9 | 3.76 | 61.2 | 3.3 | 8.3 | 9.7 | 17.5 |
| before 2059/A | 5.21 | 3.22 | 63.7 | 5.1 | 7.1 | 8.3 | 17.8 |
| after 2059/A | 5.19 | 3.28 | 65.3 | 2.4 | 6.4 | 8.2 | 17.7 |
| before 2060/A | 5.23 | 3.26 | 54.2 | 4.8 | 9.5 | 11.3 | 20.2 |
| after 2060/A | 5.20 | 3.62 | 58.3 | 3.7 | 9.7 | 10.3 | 19.0 |
| before 2060/B | 5.39 | 3.79 | 63.8 | 2.9 | 6.8 | 8.5 | 18.0 |
| after 2060/B | 5.40 | 3.57 | 64.9 | 2.7 | 7.2 | 8.5 | 16.7 |

| | Transferrin mg/dl | Ferritin ng/ml | Antithrombin III % |
|---|---|---|---|
| Plasma | 240 | 45 | 88 |
| before 2058/A | 226 | 44 | 68 |
| after 2058/A | 227 | 46 | 56 |
| before 2059/A | 244 | 41 | 61 |
| after 2059/A | 197 | 43 | 41 |

TABLE 9-continued

Protein concentrations and protein electrophoresis of the acetate-plasma mixture before and after ion exchanger 2058.83, 2059/83 and 2060/83

| before 2060/A | 212 | 50 | 72 |
|---|---|---|---|
| after 2060/A | 212 | 51 | 53 |
| before 2060/B | 207 | 48 | 70 |
| after 2060/B | 206 | 48 | 48 |

EXAMPLE 4

An adsorption trial carried out with heparin from plasma, as described in Example 3, with the use of 5 ml Lewatit ® MP 500 A, a macroporous ion exchanger by Bayer AG, Leverkusen, also produced a complete binding of the heparin and approximately 3% of the plasma proteins led through the column were bound to the anion exchanger.

EXAMPLE 5

Tests were performed to determine whether additional, known, polyanionic, heparin-like glycosamino glycans such as heparin sulfate, dermatan sulfate, heparin derivatives such as N-desulfated heparin prepared by acid hydrolysis and its derivatives and heparin fractions of varying molecular weight are also bound as is heparin, when human plasma adjusted to pH 5.1 with acetate buffer is led through an adsorber capsule equipped with Zetaprep ® fiber mats. Heparin was used as standard.

Also tested was the possible existence of differences in adsorption to the exchanger with regard to the binding properties for heparins from different sources or in dependence on the form of salt (cations) of heparin as sodium or calcium salt. Also, in the same manner, commercial heparinoids such as SP 54 ® (Bene-Chemie, Munich) and Arteparon ® (Luitpold-Werk, Munich) were tested.

Since many of these substances have no in vitro coagulation activity, an electrophoretic detection method was selected to monitor the adsorption. (H. Wohl, L. Weckly: Thrombos. Res. 30: 543–546, 1983).

The results of the adsorption tests are compiled in Table 10. The test substances were used in a concentration of 700 mg/liter acetate buffer instead of the 100,000 IU of heparin per liter of acetate buffer. The tests were performed as in Example 2, with 2,000 ml pooled human plasma and 2,000 ml acetate buffer, pH 5.1.

Figure 1:
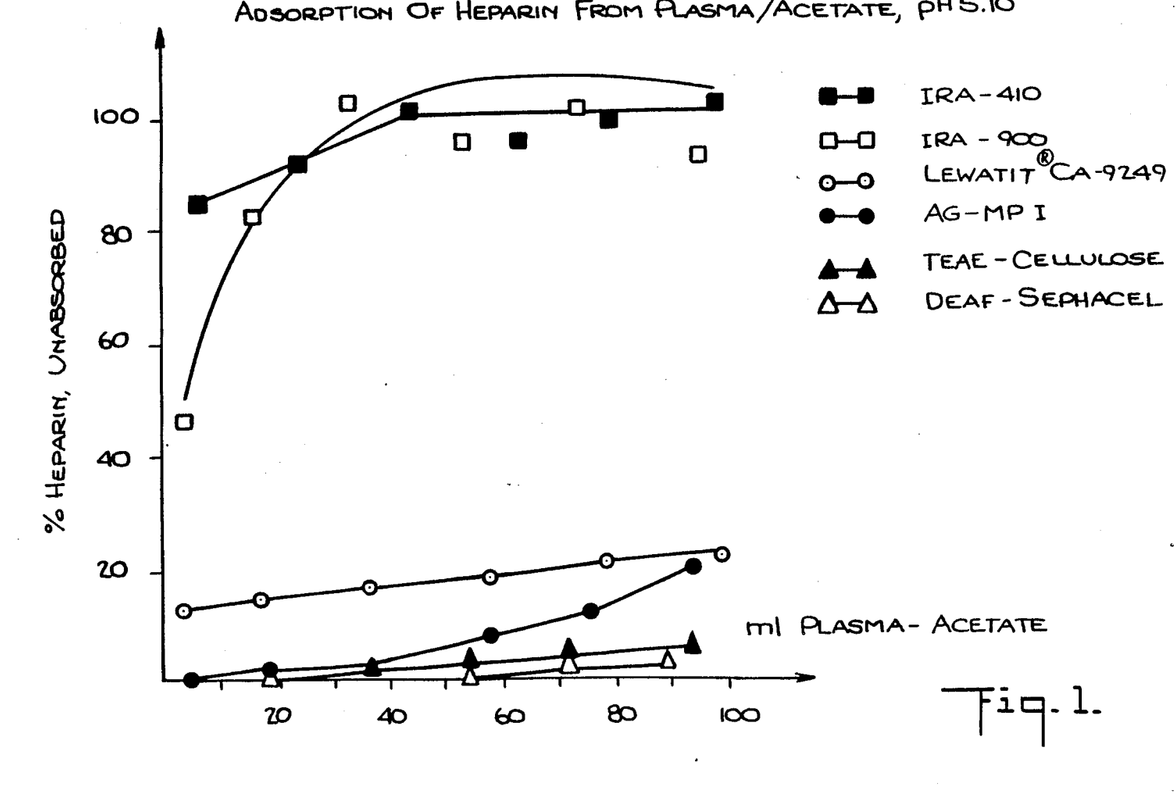
FIG. 1 is a diagram illustrating the adsorption of heparin from plasma/acetate at a pH of 5.10.

A Zetaprep® capsule DEAE 205-1 by AMF-CUNO, Meriden, Connecticut, equilibrated with 0.2M acetate buffer solution, pH 5.10 0.9% NaCl-solution (1:1 v/v) was used.

of plasma between filter 21 and the hemodialyser 26 (FIG. 1 of German Offenlegensserift DE-OS 31 35 814).

In German Offenlegensschrift DE-OS 31 35 814 wherein 2,000 ml of human plasma were employed, the

TABLE 10

Adsorption of heparin, and various heparin derivates, heparinoids, and glycosamino glycan from human plasma/acetate buffer at pH 5.1 with DEAE-Zetaprep® 250-1.

| Substance | Preparation/Source | % Adsorbed from plasma |
|---|---|---|
| Heparin-Na, commercial from pig mucosa | | 99 |
| Heparin-Ca, commercial from pig mucosa | | 99 |
| Heparin-Na, bovine lung | | 99 |
| Heparin-Na from sheep mucosa | | 98 |
| Heparin-Na from bovine mucosa | | 98 |
| Heparan sulfate, pig mucosa | Calbiochem-Behring Frankfurt | 97 |
| Dermatan sulfate | Calbiochem-Behring Frankfurt | 98 |
| Chondroitin sulfate, Type C, from shark cartilage | Calbiochem-Behring Frankfurt | 95 |
| Arteparton® (mucopolysaccharide polysulfuric acid ester) | Luitpold-Werke Munich | 95 |
| SP 54® (sodium pentosan polysulfate) | Bene Chemie, Munich | 95 |
| Heparin-Na Low molecular, MW: 4,000 prepared by degradation with HNO$_2$ according to PCT/US 81/00519 | | 99 |
| Heparin-Na, low molecular weight (5,000), prepared by degradation with heparinase from Flavobacterium heparinum | | 99 |
| Heparin-Na, high molecular weight (9,000), prepared by gel-filtration on Sephadex® G-100 from commercially available heparin-sodium-salt | | 98 |
| Heparin-Na, desulfated (an intermediate according to U.S. Pat. No. 3,118,816) | | 95 |
| Succinylated heparin, (an intermediate of German Offenlegensschrift DE-OS 31 18816 | | 95 |
| Succinylated derivate of a desulfated heparin, preparation according to: German Offenlegensschrift DE-OS 31 23 806 | | 95 |
| Chondroitin sulfate, Type A, from bovine trachea | SERVA, Heidelberg | 96 |
| Heparin, fast-moving according to: B. Casu, et al. Pharmacol. Res. Comm. 11: 297, 1979 | Calbiochem-Behring, Frankfurt | 99 |
| Heparin, slow-moving according to: B. Casu et al. Pharmacol. Res. Comm. 11, 297, 1979 | Calbiochem-Behring, Frankfurt | 99 |

EXAMPLE 6

According to the directions described in German Offenlegensscrift DE-OS 31 35 814, a Zetaprep® DEAE capsule, previously equilibrated with 0.2M sodium acetate buffer, pH 5.1, was inserted in the stream LDL precipitated as LDL-heparin complex by heparin from 2,000 ml of human plasma which was led through a heparin adsorption system (Zetaprep® 250-1) at a rate of 50 ml per minute. The total amount of heparin used in the plasma treatment was 50,000 IU per liter plasma acetate.

The LDL precipitation was tested without the heparin adsorption system in a control experiment.

Several measured values of the plasma concentration before the onset of the treatment as well as after the treatment—with and without the heparin adsorber material—are recorded in Table 11. As shown by the measured values, the content of numerous plasma constitutents is not influenced by the heparin adsorption system. The heparin concentration, in contrast, is reduced to levels that are no longer measurable.

TABLE 11

Heparin adsorption after LDL-precipitation with heparin.

| Parameter | Human plasma without treatment | Human plasma, treated without heparin adsorber material | With heparin adsorber Zetaprep ® DEAE 250-1 |
|---|---|---|---|
| Heparin | 50 IE/ml | IE/ml | 0 |
| Total protein | 6.06 g/dl | 4.62 g/dl | 470 g/dl |
| AT III | 103% | 64% | 60% |
| APO-B | 106 g/dl | 9 g/dl | 11 g/dl |
| APO-AL (=HDL) | 40.5 g/dl | not determined | 34.9 |
| Complement C3 | 100% | 50% | 50% |
| Complement C4 | 100% | 33% | 33% |
| Fibrinogen | 190 mg/dl | 0 | 0 |

The amount of protein bound to the adsorber material was far below 1% of the total protein led through the Zetaprep ® capsule.

EXAMPLE 7

The adsorption of heparin was carried out as described in Example 4. A polyamine resin prepared according to German Offenlegensschrift DE-OS 31 15 245 was used for the adsorption. A binding of 95% of the total amount of heparin was obtained, while the binding of protein was approximately 0.8%.

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

What is claimed is:

1. A process for the specific adsorption of heparin and other heparin-like substances from whole blood, plasma or diluted solutions of whole blood or plasma, which comprises the steps of:
   (a) providing a solution comprising whole blood, plasma or diluted solutions of whole blood or plasma containing heparin or other heparin-like substances;
   (b) separating corpuscular blood constituents from the solution, if necessary;
   (c) buffering the solution by means of a buffer to a pH in the range of about 4.0 to about 5.2;
   (d) flowing the buffered solution through an adsorber capsule containing a basic medium which adsorbs heparin and other heparin-like substances thereby removing heparin and other heparin-like substances from the buffered solution; and
   (e) adjusting the pH of the buffered solution to physiological conditions appropriate to a desired subject such that the solution may be infused safely into the desired subject.

2. The process according to claim 1 further comprising the steps of:
   (a) recombining the corpuscular blood constituents with the solution of step (e) adjusted to the pH appropriate to the physiological conditions of a desired subject; and
   (b) infusing the recombined solution into the desired subject or returning the recombined solution to regular stored blood.

3. The process according to claim 1 wherein the process is carried out in a closed, extracorporeal circulation.

4. The process according to claim 1 wherein the adsorber capsule comprises a sterilized, cylindrically shaped capsule containing a cap and bottom equipped with central intake and outlet nozzles and one or more circular double screens.

5. The process according to claim 4 wherein the screens have a mesh between about 50 to 100 μm.

6. The process according to claim 1 wherein the buffered solution flows through the adsorber capsule at a rate of flow between about 60 ml/hr and 25 L/hr.

7. The process according to claim 1 wherein the related heparin substances are chosen from the group consisting of heparin fractions, heparin derivatives, heparin fragments, heparinoids, and polyanionic glycosamino glycan containing sulfate ester groups.

8. The process according to claim 1 wherein the separation of the solution from corpuscular blood constituents is achieved through the use of one or more membrane plasma filters.

9. The process according to claim 1 wherein the separation of the solution from the corpuscular blood constituents is achieved through the use of a filter cascade.

10. The process according to claim 1 wherein the buffer is sodium acetate.

11. The process according to claim 1 wherein the buffered solution has a pH between about 4.7 and 5.2.

12. The process according to claim 1 wherein the buffered solution flows through the absorber capsule at a rate of flow between about 1.5 and 12 L/hr.

13. The process according to claim 1 wherein the medium of the adsorber capsule is selected from the group consisting of an ion exchange resin acting as an anion exchanger and a macroporous anion exchange resin possessing basic anchor groups.

14. The process according to claim 1 wherein the adsorber capsule is equipped with an adsorption filter cartridge.

15. The process according to claim 1 wherein the adsorber capsule contains an adsorption filter cartridge comprising a supporting screen with a solid or hollow core, around which screen is wound a fiber mat on a cellulose base that possesses anion exchange properties thereby capable of acting as an active adsorber material.

16. The process according to claim 1 wherein the adsorber capsule is filled with a gel possessing anion exchange properties and which is moistened with water.

17. The process according to claim 1 wherein the adsorber capsule has a heparin capacity between about 10,000 and 100,000 IU of heparin, and a capacity for heparinoids, heparin fractions, heparin fragments and heparin derivatives of about 2 grams.

18. The process according to claim 1 wherein the adsorber capsule is sterilized by a method selected from the group consisting of exposure to gamma rays, treatment with ethylene oxide and heat treatment prior to the flowing of the buffered solution through the adsorber capsule.

19. A process for the specific adsorption of heparin and other heparin-like substances from whole blood, plasma or diluted solutions of whole blood or plasma, which comprises the steps of:
 (a) providing a solution comprising plasma or diluted solutions of plasma containing heparin or other heparin-like substances;
 (b) separating corpuscular blood constituents from the solution, if necessary;
 (c) buffering the solution by means of a buffer to a pH in the range of about 4.7 to about 5.2;
 (d) flowing the buffered solution through an adsorber capsule containing a basic anion exchanger adsorption material which adsorbs heparin and other heparin-like substances;
 (e) adjusting the pH of the buffered solution to physiological conditions appropriate to a desired subject, such that a solution by safely be infused into the desired subject.

20. The process according to claim 19 wherein the other heparin-like substances are selected from the group consisting of heparin fractions, heparin fragments, heparin derivatives, heparinoids and polyanionic glycosamino glycan containing sulfate ester groups.

21. The process according to claim 19 further comprising the steps of:
 (a) recombining the corpuscular blood constituents with the solution of step (e) adjusted to the pH appropriate to the physiological conditions of a desired subject; and
 (b) infusing the recombined solution into the desired subject or returning the recombined solution to regular stored blood.

22. The process according to claim 19 wherein the medium of the adsorber capsule is selected from the group consisting of an ion exchange resin acting as an anion exchanger and a macroporous anion exchange resin possessing basic anchor groups.

23. The process according to claim 19 wherein the process is carried out in a closed, extracorporeal circulation.

24. The process according to claim 19 wherein the adsorber capsule comprises a sterilized, cylindrical shaped capsule containing a cap and bottom equipped with central intake and outlet nozzles and one or more circular double screens.

25. The process according to claim 24 wherein the screens have a mesh between about 50 to 100 $\mu$m.

26. The process according to claim 19 wherein the buffered solution flows through the adsorber capsule at a rate of flow between about 60 ml/hr and 25 L/hr.

27. The process according to claim 19 wherein the solution may be whole blood or diluted solutions of whole blood.

28. The process according to claim 19 wherein the related haparin substances are chosen from the group consisting of heparin fractions, heparin derivatives, heparin fragments, heparinoids, and polyanionic glycosamino glycan containing sulfate ester groups.

29. The process according to claim 19 wherein the separation of the solution from corpuscular blood constituents is achieved through the use of one or more membrane plasma filters.

30. The process according to claim 19 wherein the separation of the solution from the corpuscular blood constituents is achieved through the use of a filter cascade.

31. The process according to claim 19 wherein the buffer is sodium acetate.

32. The process according to claim 19 wherein the buffered solution flows through the adsorber capsule at a rate of flow between about 1.5 and 12 L/hr.

33. The process according to claim 19 wherein the adsorber capsule is equipped with an adsorption filter cartridge.

34. The process according to claim 19 wherein the adsorber capsule contains an adsorption filter cartridge comprising a supporting screen with a solid or hollow core, around which screen is wound a fiber mat on a cellulose base which possesses anion exchange properties capable of acting as an active adsorber material.

35. The process according to claim 19 wherein the adsorber capsule is filled with a gel possessing anion exchange properties and which is moistened with water.

* * * * *

UNITED STATES PATENT AND TRADEMARK OFFICE
CERTIFICATE OF CORRECTION

PATENT NO. : 4,935,204          Page 1 of 2

DATED : June 19, 1990

INVENTOR(S) : Dietrich Seidel, et al.

It is certified that error appears in the above-identified patent and that said Letters Patent is hereby corrected as shown below:

Column 1, line 59, change "Sicence" to -- Science--

Column 2, line 38, change "absorption" to --adsorption--

Column 3, line 17, change "flow" to --flows--

Column 4, line 16, change "fragments" to --fragments,"

line 23, change "substacnes" to --substances"

line 40, change "substacnes" to --substances"

Column 8, line 25, change "in the these" to --in these--

Column 9, Table 6, line 1, change "250-2" to --250-3--

Table 6, Col.: Cholesterol g/L, 6th entry,
                   change "0.43" to --0.42--

Column 11, line 50, change "2058.83" to --2058/83--

UNITED STATES PATENT AND TRADEMARK OFFICE
CERTIFICATE OF CORRECTION

PATENT NO. : 4,935,204

DATED : June 19, 1990

INVENTOR(S) : Dietrich Seidel, et al.

It is certified that error appears in the above-identified patent and that said Letters Patent is hereby corrected as shown below:

Column 12, line 11, change "2058.83" to --2058/83--

Column 13, line 3, change "pH 5.10 0.9%" to --pH 5.10, 0.9%--

Column 14, line 2, change "Offenlegensserift" to --Offenlegensschrift--

Column 15, line 17, change "IE/ml" to --23 IE/ml--

Column 16, line 55, change "absorber" to --adsorber--

Column 17, line 35, change "by" to --may--

Signed and Sealed this

Twenty-third Day of June, 1992

Attest:

DOUGLAS B. COMER

*Attesting Officer*     Acting Commissioner of Patents and Trademarks